United States Patent [19]

Hedberg

[11] Patent Number: 5,476,484
[45] Date of Patent: Dec. 19, 1995

[54] APPARATUS FOR SENSING A PHYSICAL CONDITION IN A LIVING SUBJECT

[75] Inventor: Sven-Erik Hedberg, Kungsängen, Sweden

[73] Assignee: Pacesetter AB, Solna, Sweden

[21] Appl. No.: 338,090

[22] Filed: Nov. 9, 1994

[30] Foreign Application Priority Data

Nov. 12, 1993 [SE] Sweden .................. 9303736

[51] Int. Cl.⁶ .................................................... A61B 5/02
[52] U.S. Cl. ........................... 607/23; 607/21; 128/672
[58] Field of Search ................... 128/672, 668,
128/691, 667, 687, 661.08, 677, 680–682;
607/21, 22, 23, 17, 24

[56] References Cited

U.S. PATENT DOCUMENTS

| | | |
|---|---|---|
| 4,030,485 | 6/1977 | Warner ..................... 128/672 |
| 5,014,715 | 5/1991 | Chapolini ................. 128/672 |
| 5,054,493 | 10/1991 | Cohn et al. . |
| 5,081,988 | 1/1992 | Cook et al. ................. 607/21 |
| 5,099,852 | 3/1992 | Meister et al. . |

FOREIGN PATENT DOCUMENTS

| | | |
|---|---|---|
| 0178528 | 4/1986 | European Pat. Off. . |
| 0330463 | 2/1989 | European Pat. Off. ........ 128/661.08 |
| 0474958 | 3/1992 | European Pat. Off. . |

Primary Examiner—Angela D. Sykes
Assistant Examiner—Stephen Huang
Attorney, Agent, or Firm—Hill, Steadman & Simpson

[57] ABSTRACT

An apparatus for determining a physical condition in a living subject by determining peripheral resistance to flow is wherein peripheral resistance to flow is determined by measuring changes in the pressure drop characteristic in an artery during diastole. The pressure drop characteristic can be determined by measuring absolute pressure, relative pressure or dimensional changes in the artery during diastole. The apparatus can advantageously be used in a rate-responsive heart stimulator.

12 Claims, 2 Drawing Sheets

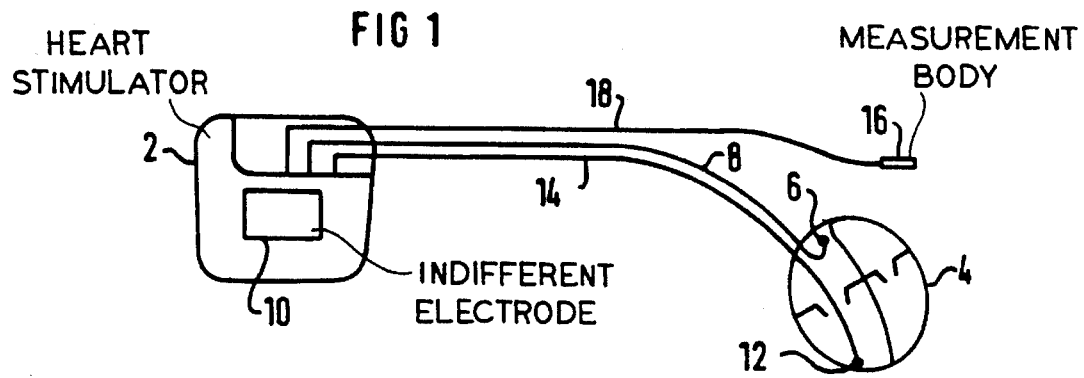
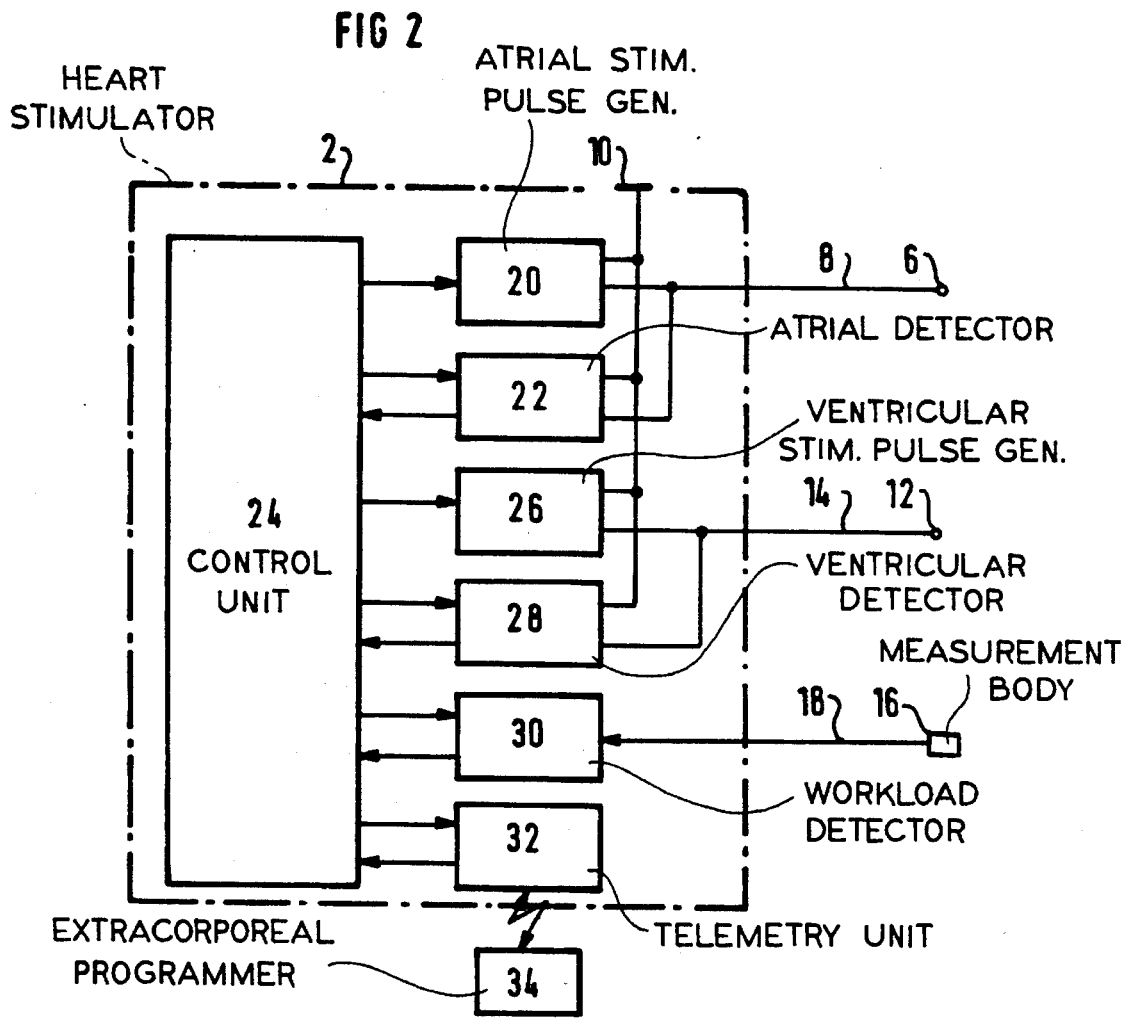

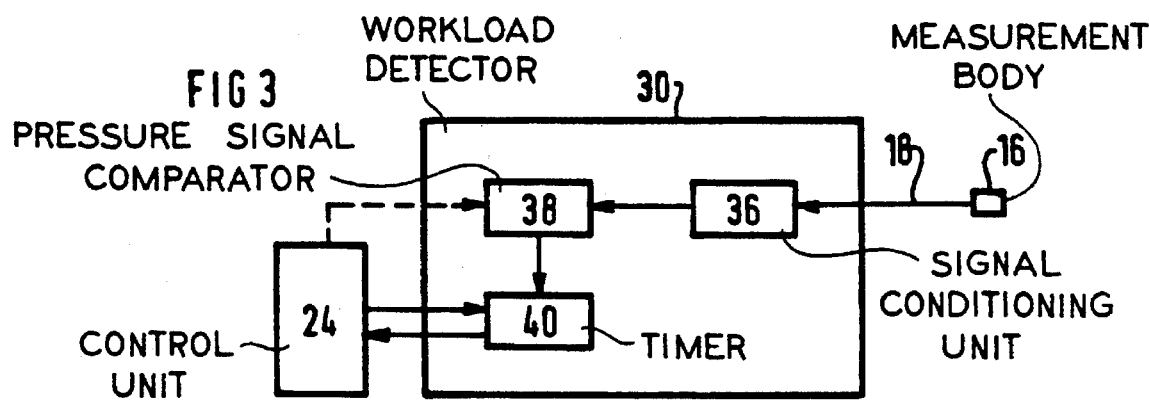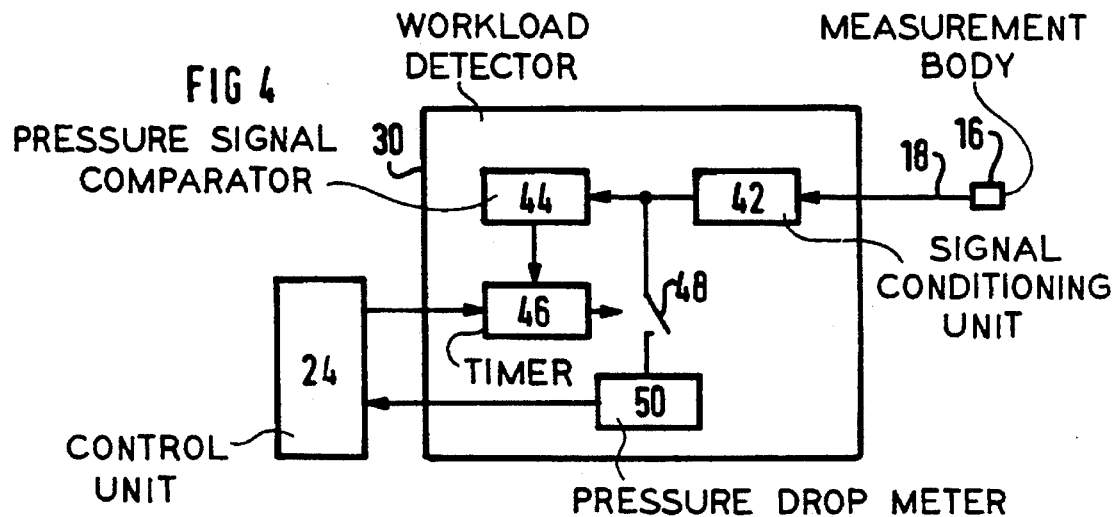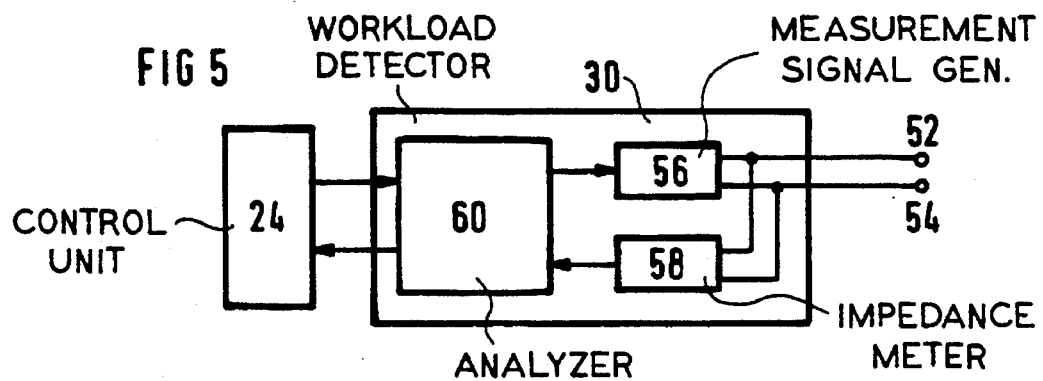

5,476,484

APPARATUS FOR SENSING A PHYSICAL CONDITION IN A LIVING SUBJECT

BACKGROUND OF THE INVENTION

1. Field of the Invention

The present invention is directed to an apparatus for sensing a physical condition in a living subject of the type having a sensor for acquiring a measurement signal related to blood pressure in the subject.

The invention also relates to a rate-responsive heart stimulator.

2. Description of the Prior Art

For people with various pathological heart conditions or functional defects in different tissues, the heart in particular, measured indications of the patient's state of health constitute desirable information. It is also desirable to have the ability to stimulate the functioning of the heart of patients with heart problems, so the functioning of a healthy heart is simulated as accurately as possible.

As used herein, "physical condition" refers to both the general state of health of the subject as well as the workload (activity level) of the subject, i.e., whether the subject is at rest or under light or heavy physical strain.

Blood pressure is a parameter which reflects a person's state of health and which can also be utilized for controlling a heart stimulator's stimulation of a heart.

In European Application 0 178 528 a heart stimulator is disclosed which can stimulate a heart at a variable rate according to systolic peak pressure or its time derivative. Here, a pressure sensor is placed in the right ventricle to measure blood pressure. Systolic pressure increases when the patient's level of physical activity increases, and an appropriate stimulation rate can be set according to the peak pressure value or the time derivative of pressure.

Systolic pressure is, however, a heart parameter which does not solely depend on the patient's degree of physical exertion, but also is affected by other factors, such as stress, body position etc. In addition, there are natural variations in the systolic pressure of patients. This means that systolic pressure is not a particular appropriate parameter for use in attaining the most natural variation in stimulation rate possible.

SUMMARY OF THE INVENTION

One object of the invention is to achieve an apparatus for sensing a physical condition related to blood pressure in a way which avoids the aforesaid problems.

Another object of the invention is to achieve a rate-responsive heart stimulator which stimulates the heart at the most natural rate possible.

The first object is achieved in accordance with the invention in an apparatus having an analyzer for determining peripheral resistance to flow in the living subject by determining a pressure drop characteristic for the drop in blood pressure in an artery during diastole on the basis of the measurement signal.

Peripheral resistance supplies a better measure of a person's physical condition, in particular a better measure of a person's degree of physical exertion, than does blood pressure. Peripheral resistance affects the reduction or drop in arterial pressure during diastole. In principle, the drop in arterial pressure is exponential. Determination of the characteristic, or the time constant, for the pressure drop results in accurate determination of peripheral resistance.

Preferably, therefore, the analyzer includes a timer for measuring the duration for the drop in blood pressure from a first blood pressure level to a second blood pressure level.

In this way, the time constant can be determined for the drop in pressure between two blood pressure levels. Preferably the first blood pressure is the blood pressure at the beginning of diastole and the second blood pressure is the blood pressure at the end of diastole.

Alternatively, the apparatus can be devised so the analyzer determines the drop in blood pressure over a preset time interval during diastole.

Since the pressure drop characteristic is governed by the drop in pressure and the time required for the pressure to drop, the drop in pressure over a preset interval can reflect the pressure drop characteristic in the same way as a measurement of the time required for the pressure to drop from one blood pressure level to another.

In an embodiment of the apparatus in accordance with the invention the sensor is a pressure-sensitive measurement body, devised for placement in an artery, for sensing the blood pressure.

The pressure drop characteristic can be determined in any artery in the body. The most appropriate location for the measurement body should be decided upon from case to case. Some sites which may be referable are, e.g., the aorta, the carotid artery or the subclavian artery.

It is, in connection with the above embodiment, advantageous if the pressure-sensitive body is devised to sense relative changes in pressure.

In principle, the pressure drop characteristic is completely independent of absolute blood pressure and it is therefore fully sufficient only to determine relative changes in pressure in the blood circulation, which is simpler than measuring absolute pressure.

In an alternative embodiment of the apparatus in accordance with the invention the sensor is an impedance meter, devised for placement in or near an artery, preferably the aorta, in order to measures changes in the dimensions of the artery, these dimensional changes corresponding to changes in pressure in the artery.

No measurement of pressure is actually necessary in this embodiment. As a result of the elastic properties of the arteries, the dimensions of the arteries change when pressure changes. Measuring these dimensional changes also supplies a measure of relative changes in pressure. Measurement of impedance is an effective method for determining these dimensional changes. Impedance can be measured inside the artery itself or from the outside of the artery.

The second object is achieved in accordance with the invention in a rate-responsive heart stimulator, having a stimulation pulse generator for generating and emitting stimulation pulses to a heart at a variable stimulation rate, a detector for sensing physical workload in a living being and a control device for controlling the stimulation rate of the stimulation pulse generator according to the workload sensed by the detector, with the detector being constructed and operating according to one of the above-described embodiments.

DESCRIPTION OF THE DRAWINGS

FIG. 1 shows a rate-responsive heart stimulator includes a detector constructed and operating according to the invention.

FIG. 2 is in a block diagram showing components of the heart stimulator of FIG. 1 in greater detail.

FIG. 3 is a block diagram of a first embodiment of a detector constructed and operating in accordance with the principles of the present invention.

FIG. 4 is a block diagram of a second embodiment of a detector constructed and operating in accordance with the principles of the present invention.

FIG. 5 is a block diagram of a third embodiment of a detector constructed and operating in accordance with the principles of the present invention.

DESCRIPTION OF THE PREFERRED EMBODIMENTS

A heart stimulator 2 is connected, as shown in FIG. 1, to a heart 4 in order to stimulate the heart 4. An atrial electrode 6 is anchored in the right atrium of the heart and connected, via a first electrode conductor 8, to the heart stimulator 2. A stimulation pulse can be generated by the heart stimulator 2 and delivered to the heart 4 via the first electrode conductor 8 and the atrial electrode 6. The stimulation pulse then returns to the heart stimulator 2 via body tissue and an indifferent electrode 10. A ventricular electrode is anchored in the right ventricle of the heart 4 and is connected to the heart stimulator 2 via a second electrode conductor 14. In the corresponding manner as for the atrium, the heart stimulator 2 can stimulate the ventricle by emitting a stimulating pulse through the second electrode conductor 14 and the ventricular electrode 12. Even in this instance, the stimulation pulse returns to the heart stimulator 2 via body tissue and the indifferent electrode 10.

For stimulation of the heart in a way which simulates the natural beat of a healthy heart, a pressure-sensitive measurement body 16 is placed in an artery outside the heart 4 to sense the pressure. In principle, the measurement body 16 can be placed in any artery. The measurement signal is sent to the heart stimulator 2 via a measurement signal line 18. On the basis of the measurement signal, the heart stimulator 2 can ascertain the patient's level of physical exertion and therefore regulate the stimulation rate in a way described below.

The construction of the heart stimulator 2 is shown in greater detail in the block diagram in FIG. 2. An atrial stimulation pulse generator 20 is connected to the atrial electrode 6 and the indifferent electrode 10. The atrial stimulation pulse generator 20 generates and emits stimulation pulses with a programmable amplitude and duration. An atrial detector 22 is connected in parallel across the output terminal of the atrial stimulation pulse generator 20 to sense spontaneous responses in the atrium. An atrial stimulation pulse can be inhibited if the atrial detector 22 senses a spontaneous atrial event. As a result no unnecessary stimulation pulses, which are uncomfortable to the patient, are emitted, and the power consumption of the heart stimulator 2 is reduced. The atrial stimulation pulse generator 20 and the atrial detector 22 are controlled by a control unit 24 which also receives signals from the atrial detector 22 when a spontaneous atrial event has occurred. The control unit 24 regulates the emission of stimulation pulses by the stimulation pulse generator 20.

In a corresponding manner, a ventricular stimulation pulse generator 26 is connected to the ventricular electrode 12 and the indifferent electrode 10. A ventricular detector 28 is connected in parallel across the output terminal of the ventricular stimulation pulse generator 26 to sense spontaneous ventricular events. A ventricular stimulation pulse can be inhibited when a spontaneous ventricular event occurs.

Thus, the heart stimulator 2 senses the heart 4 for the occurrence of spontaneous events, and no stimulation pulses are emitted as long as the heart functions normally. The heart stimulator 2 is equipped with a workload detector 30 for determining whether the heart operates at an adequate rate even during physical exertion and for stimulating the heart 4 at an adequate rate during physical exertion. The workload detector 30 is connected to the pressure-sensitive measurement body 16 and processes the measurement signal obtained via the measurement signal line 18 in order to determine the level of exertion of the person in whom the heart stimulator is implanted. The control unit 24 receives a signal from the detector 30 which can be transformed into a stimulation rate. The control unit 24 can also control the workload detector 30 and/or supply it with other parameters.

The heart stimulator 2 can, via a telemetry unit 32, transmit and receive information to/from an extracorporeal programming unit 34. A physician thereby can read out how the heart stimulator 2 has operated with the prevailing programming and the therapy supplied and determine how well the patient's heart 4 has operated spontaneously. The physician can also re-program the heart stimulator 2 in order to improve the performance of the heart stimulator 2.

FIG.3 shows a first example of the way in which the workload detector 30 can be devised in order to determine the subject's level of activity. A measured pressure signal is sent from the measurement body 16, via the measurement signal line 18, to a signal conditioning unit 36 in the detector 30. The pressure signal from the signal conditioning unit 36 is compared in a pressure signal comparator 38 with two pressure levels. When the pressure signal drops below the first pressure level, a timer 40 is activated which measures the time it takes pressure to drop by a specific amount, governed by the two pressure levels. When the pressure signal falls below the second pressure level, therefore, the timer 40 stops, and the time measured is sent to the control device 24 which selects, by means of an algorithm or a table, a corresponding stimulation rate. The two pressure levels can be regulated by the control unit 24.

As an alternative to measurement between two preset pressure levels, the measurement body 16 can be devised so it only senses the relative change in pressure, and the pressure signal comparator 38 is devised to activate the timer 40 at peak pressure and stop the timer 40 at nadir (lowest) pressure, the pressure drop during diastole constituting the pressure level for which the pressure drop time is determined.

FIG. 4 shows another version of the workload detector 30 for determining the subject's level of physical activity. As in the preceding instance, a measurement signal is sent from the measurement body 16 via a measurement signal line 18 to a signal conditioning unit 42. The pressure signal is then sent to a pressure signal comparator 44 which activates a timer 46 when the pressure signal is less than a preset pressure level or exceeds its peak value. The timer 46 closes a switch 48 for a programmable period of time. When the switch 48 is closed, the pressure signal is sent to a pressure drop meter 50 which measures the drop in pressure during the preset interval. The pressure drop thus obtained is sent to the control unit 24 for conversion to a stimulation rate. The control unit 24 can change the timing interval of the timer 46. The measured drop in pressure over a preset interval supplies a pressure drop characteristic which is equivalent to the one obtained when the time for a specific pressure drop is measured.

FIG. 5 shows an additional, alternative version of the workload detector 30. A signal is passed between a first electrode 52 and a second electrode 54 from a measurement signal generator 56. The signal is devised to measure impedance between the first electrode 52 and the second electrode 54 with an impedance meter 58. When the electrodes 52 and 54 are placed so they measure dimensional changes in, e.g., the aorta, the measured impedance is equivalent to changes in pressure in the aorta. The impedance signal thus obtained is sent to an analyzer 60 for additional signal conditioning. This process can be accomplished as described previously, i.e., the changes in impedance can be used for determining the pressure drop characteristic during diastole, and used for establishing the subject's level of activity and for determining a stimulation rate. The analyzer 60 communicates with the control unit 24.

The described heart stimulator can be devised with bipolar electrodes instead of unipolar electrodes. The detector 30 can be incorporated in all types of known heart stimulators, including pacemakers, cardioverters and defibrillators, in order to sense the subject's level of activity.

Although modifications and changes may be suggested by those skilled in the art, it is the intention of the inventor to embody within the patent warranted hereon all changes and modifications as reasonably and properly come within the scope of his contribution to the art.

I claim as my invention:

1. A rate-responsive heart stimulator comprising:

a housing adapted for implantation in a living subject;

stimulation pulse generator means, contained in said housing, for generating and delivering stimulation pulses to a heart of said subject at a variable stimulation rate;

control means in said housing for controlling said stimulation rate dependent a physical workload of said subject; and detector means for sensing said physical workload comprising sensor means, adapted for placement in an artery of said subject, for acquiring a measurement signal related to blood pressure in a subject, and analyzer means, contained in said housing and supplied with said measurement signal, for determining a peripheral resistance to blood flow in said subject by identifying a pressure drop characteristic from said measurement signal for a drop in blood pressure in an artery during diastole and for supplying an electrical signal corresponding to said peripheral resistance to blood flow to said control means as indicative of said physical workload and said control means controlling said stimulation rate dependent on said peripheral resistance to a blood flow.

2. An apparatus as claimed in claim 1 wherein said analyzer means comprises timer means for measuring a duration for a drop in said blood pressure from a first blood pressure level to a second blood pressure level.

3. An apparatus as claimed in claim 2 wherein said analyzer means comprises timer means for measuring a duration for a drop in said blood pressure from a first blood pressure level at a beginning of diastole to a second blood pressure level at an end of diastole.

4. An apparatus as claimed in claim 3 wherein said sensor means comprises a pressure-sensitive measurement body for sensing said blood pressure.

5. An apparatus as claimed in claim 4 wherein said pressure-sensitive measurement body comprises means for sensing relative changes in said blood pressure.

6. An apparatus as claimed in claim 1 wherein said analyzer means comprises means for determining a drop in said blood pressure over a preset time interval during diastole.

7. An apparatus as claimed in claim 6 wherein said sensor means comprises a pressure-sensitive measurement body for sensing said blood pressure.

8. An apparatus as claimed in claim 7 wherein said pressure-sensitive measurement body comprises means for sensing relative changes in said blood pressure.

9. An apparatus as claimed in claim 6 wherein said sensor means comprises an impedance meter, for measuring changes in dimensions of said artery, said changes in dimensions corresponding to changes in blood pressure in said artery.

10. An apparatus as claimed in claim 1 wherein said sensor means comprises an impedance meter for measuring changes in dimensions of said artery, said changes in dimensions corresponding to changes in blood pressure in said artery.

11. An apparatus as claimed in claim 10 wherein said analyzer means comprises timer means for measuring a duration for a drop in said blood pressure from a first blood pressure level to a second blood pressure level.

12. An apparatus as claimed in claim 11 wherein said analyzer means comprises timer means for measuring a duration for a drop in said blood pressure from a first blood pressure level at a beginning of diastole to a second blood pressure level at an end of diastole.

* * * * *